United States Patent [19]

Moran et al.

[11] Patent Number: 4,744,656
[45] Date of Patent: May 17, 1988

[54] DISPOSABLE CALIBRATION BOOT FOR OPTICAL-TYPE CARDIOVASCULAR CATHETER

[75] Inventors: Byron L. Moran, Santa Barbara; Allan F. Willis, Newbury Park, both of Calif.; Mendelson, Yitzhak, Worcester, Mass.

[73] Assignee: Spectramed, Inc., Oxnard, Calif.

[21] Appl. No.: 939,009

[22] Filed: Dec. 8, 1986

[51] Int. Cl.$^4$ .............................................. G01J 1/02
[52] U.S. Cl. .................................... 356/243; 356/41; 356/42
[58] Field of Search ................... 356/39, 40, 41, 42, 356/243; 250/252.1; 128/632, 633, 634, 637

[56] References Cited

U.S. PATENT DOCUMENTS

| | | | |
|---|---|---|---|
| 4,050,450 | 9/1977 | Polanyi et al. | 356/243 X |
| 4,322,164 | 3/1982 | Shaw et al. | 356/243 |
| 4,650,327 | 3/1987 | Ogi | 356/243 |

Primary Examiner—Eugene R. Laroche
Assistant Examiner—Robert J. Pascal
Attorney, Agent, or Firm—Ashen Golant Martin & Seldon

[57] ABSTRACT

The catheter tip fits into a cavity in the boot and is held gently (in the longitudinal direction) by a detent formed within the cavity. A calibration substance faces the tip in a mechanically and optically standardized calibration relationship, to reflect light from within the catheter back into the catheter. The calibration substance is held in constant, precise contact with the tip—but passively, not by springs or other longitudinally forcible devices but by close fit between the tip and the precision-molded internal surfaces of the cavity. In the lateral direction the boot may tightly grip the tip, at a point where the optic fibers are protected against such force. To provide a reflection standard for calibration, the calibration substance is of standardized character and quality: it is preferably a homogeneous suspension of reflecting particles in translucent or transparent polymer. The entire boot is preferably compression- or injection-molded from the calibration substance, except for a rigid, opaque outer skin. The catheter is shipped to a customr with the boot in place, ready for calibration on receipt or whenever thereafter the catheter is to be used. After calibration the boot is removed and discarded.

13 Claims, 2 Drawing Sheets

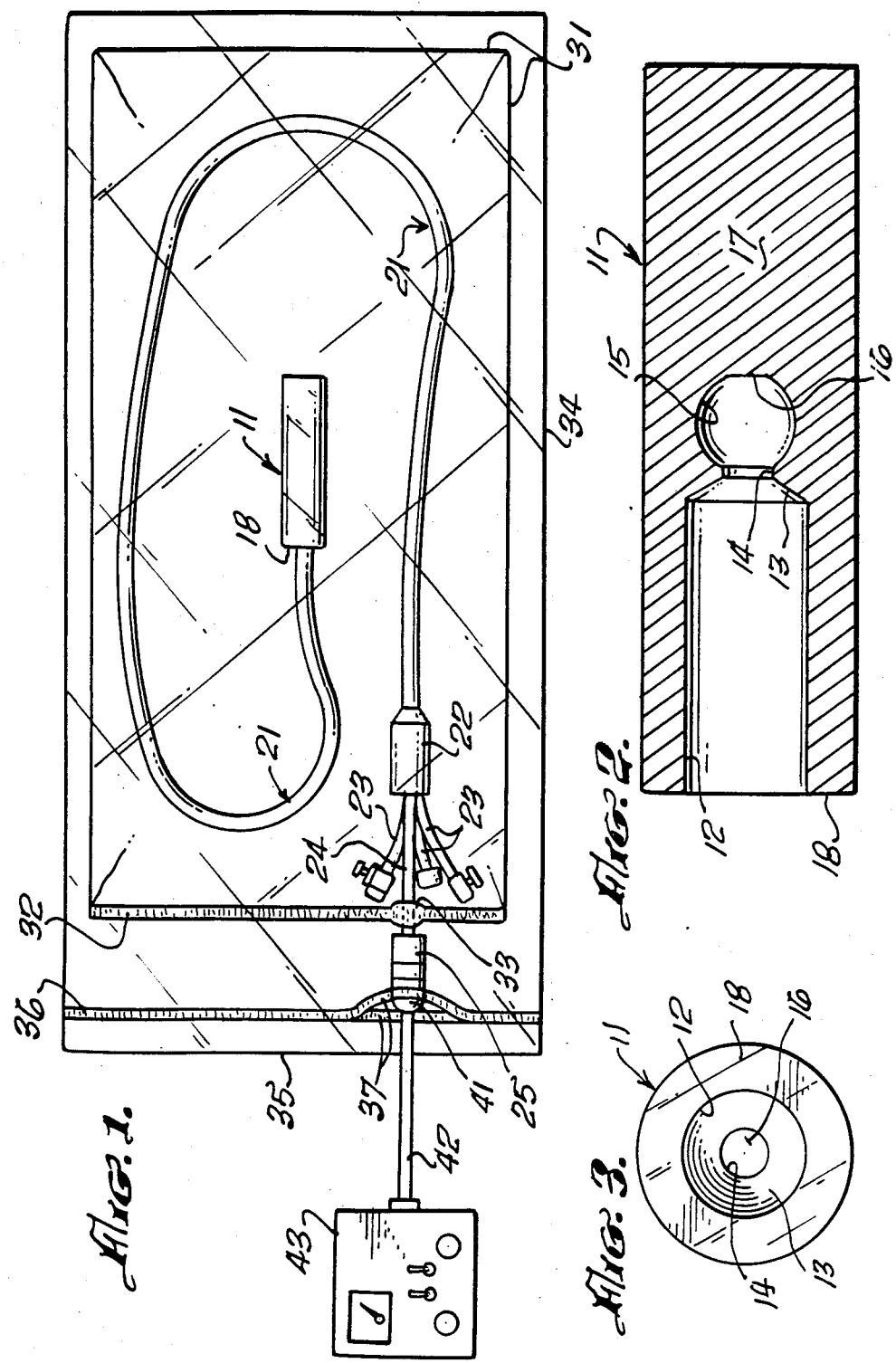

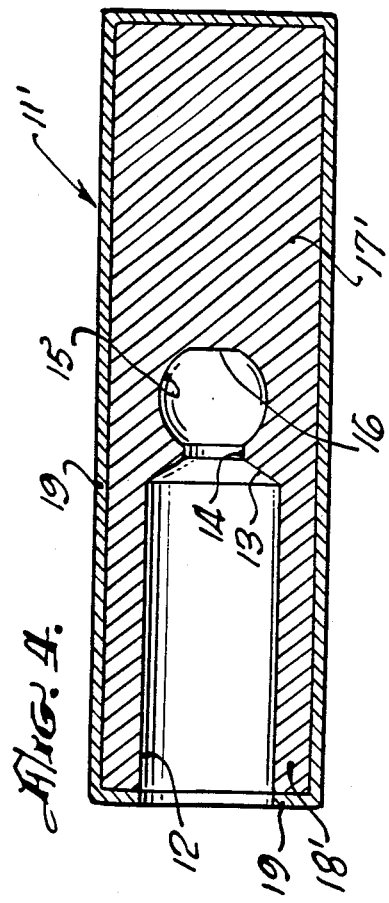
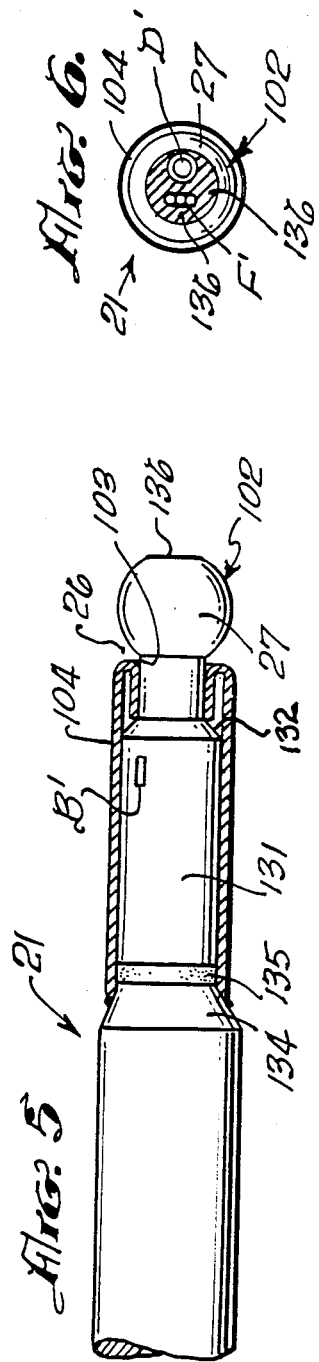

DISPOSABLE CALIBRATION BOOT FOR OPTICAL-TYPE CARDIOVASCULAR CATHETER

BACKGROUND 1. Field Of The Invention

This invention relates generally to cardiovascular catheters of the type that include optical fibers for spectrometric determination of oxygen saturation or other chemical parameters of blood, and more particularly to a disposable calibration medium and shipping sleeve for such a catheter.

2. Prior Art

It has been recognized for some decades that such cardiovascular catheters of the optical type require calibration to compensate for variations in several parameters—particularly including transmission efficiency of fibers at multiple wavelengths, distance between fibers at the catheter tip, efficiency of optical connectors, and variations in gain of the detectors receiving back-scattered light from the fibers.

Therefore it is necessary to match a catheter to an electrooptical instrument, and calibrate the overall system as a unit. The catheter is connected to the instrument and the catheter tip exposed to a reference medium providing a known amount of back-scatter reflection; the instrument is calibrated; and the catheter then is separated from the reference medium and inserted into the fluid (usually blood) to be measured.

The historical technique for accomplishing the calibration step is to immerse the catheter tip into a reference liquid that contains suspended particles to reflect light back into the catheter. A standard used since the 1950s has been milk of magnesia—that is, a suspension of magnesium oxide.

This technique is subject to disadvantages. It is inconvenient to the user. It places severe sterility requirements on the calibrating liquid. It is hazardous to the patient or research subject, due to potential toxicity of traces of the liquid on the catheter when the catheter is subsequently placed in a living body. All these problems are attributable to the use of a liquid as the standard.

To avoid these problems Polyani et al. (U.S. Pat. No. 4,050,450) proposed using a hollow tube as a calibrating device. Conceptually this proposal has merit since it inherently avoids contact of the catheter tip with a liquid.

One of the present inventors, however, has tested this technique and found it objectionably imprecise—that is, not adequately repeatable. We cannot account entirely for the observed imprecision, though it is likely related to the difference between reflection properties of a smooth plastic wall and reflection properties of a particle suspension in a liquid medium such as blood.

Shaw et al. (U.S. Pat. No. 4,322,164) have described a calibration system using reflecting particles suspended in a transparent solid polymeric medium as an optical calibration standard. A spring presses the surface of the polymer against the catheter tip.

In the Shaw system, a latch mechanism holds the calibration surface out of contact with the catheter tip until the time for calibration. Then the user unlocks the latch mechanism (by actuating a release device manually through a sterile envelope), allowing the spring to push the calibration surface across a short gap into contact with the catheter tip.

Shaw's innovation represents an important step forward in this technology. His suspension of particles in a transparent solid medium offers substantial promise of simulating quite closely the reflection properties of blood. Shaw, like Polyani, avoids using a liquid as the calibration standard.

Thus the Shaw patent presents an ingenious and very useful solution to a knotty problem. Nevertheless that solution has its own drawbacks—particularly with regard to the mechanics of use—and so leaves considerable room for refinement.

These drawbacks will first be enumerated, and then discussed in detail. First, the Shaw device is needlessly elaborate mechanically. Secondly, it virtually prevents prechecking the calibration or even the general integrity of the optics after packaging but before final use.

Thirdly, Shaw's device is somewhat awkward in use because it must be actuated through the sterile container. Fourthly, it is subject to measurement errors that can arise from this procedure.

Finally, it places potentially conflicting requirements on the physical properties of the suspension medium. We will now take up each of these points in turn.

First as to the mechanical elaborateness or complexity of the Shaw device, that complexity includes providing:

(a) a movable gripper that holds the catheter in place by friction (after it is positioned within the overall device), (b) a separate movable plunger that carries the calibration surface into contact with the catheter, (c) a mechanical track along which the plunger can move (and it must move reliably), (d) a spring for impelling the plunger along the track to bring the calibration surface into contact with the catheter tip with a reliably predetermined force, (e) a latch to prevent the plunger from moving until desired, and (f) a rocker arm that increases the lateral grip on the catheter at the last instant before the plunger is allowed to move.

All this must be accomplished without compromising the light-tight character of the entire unit, and of course without materially increasing the cost of the catheter.

Turning secondly to the desirability of prechecking calibration (or even prechecking the general operability of the optical-fiber subsystem): the Shaw invention deters such prechecking because the latch-release mechanism is designed to "fire" just once.

It would be desirable to have a means of verifying continuing integrity of the catheter if it remains in storage for a long time in the manufacturer's warehouse. Such verification, within the manufacturer's premises, could even include verifying stability of calibration, since the same instrument could be used for initial and all subsequent checks.

It would also be desirable to have a means of verifying continuing integrity of the catheter if it remains in storage for a long time in an intermediate wholesaler's warehouse. Here again, stability of calibration could be verified within that facility.

It would be even more desirable to have a means of verifying the integrity of a catheter upon arrival in the storeroom of the hospital or research facility where it is to be used. In this way the usability of a stock of catheters could be guaranteed against the rigors of long-distance shipment.

It is only very minimally useful to conduct such verifications when the catheters are drawn out of the storeroom for use, for at that point a timely replacement may be impossible. It will be understood that stability of calibration could be checked in this context as well.

In principle, for later reuse Shaw's plunger could be pulled back out and the latch reseated. Such a procedure, however, would be tricky to perform through the sterile container—at least without compromising the positional accuracy of the catheter tip in the calibration device.

That brings us to the third drawback: awkwardness in use through the sterile container. The Shaw device must be actuated by pressing in on the rocker arm, to increase the gripping force on the catheter and simultaneously release the latch that restrains the spring-loaded plunger.

As a practical matter, however, "pressing in on the rocker arm" in this context means squeezing the portion of the device where the rocker arm is accessible. Otherwise the entire device will simply slide away from the user's finger.

In order to squeeze the device, one must grip it between thumb and forefinger. Depending upon the initial orientation of the device in its package, this may require either that the user somehow position the thumb or forefinger (working through the sterile container) beneath the device, or that the device be rotated in its shipping tray so that the direction of motion of the rocker is generally horizontal.

Therefore the user must be very nimble-fingered, or the device must be held on the tray by a formed mount (yet another elaboration, and one that would increase the potential for damage during shipment), or in preparation for squeezing the rocker the user must rotate the device with the other hand, again through the sterile container.

During any of these operations, of course, there is a constant risk of rupturing the container and thereby exposing the catheter to contamination. It is not our intention to make more of this awkwardness than there is, but it will be apparent that use of the Shaw device is not completely without pitfalls.

The fourth drawback mentioned above is the potential for measurement error arising from the cumbersome manipulation of the calibration device through the sterile container. This is a more complicated matter to discuss.

On one hand, there may be means for mitigating the awkwardness of operation. Such means may include a reasonably reliable preorientation of the device in its package, and/or extraordinary dexterity on the part of the user. These factors may "save" the Shaw device from the inherent awkwardness discussed above.

Furthermore, awkwardness in use is in a sense self-limiting. The user can determine clearly—by direct visual observation, coupled with taking a calibration reading—whether he or she has been successful in releasing the latch.

On the other hand, such a "save" may yet leave a drawback that is even more problematical, due to being hidden. The user in fumbling with the device to rotate it into position for operation, or in the actual step of releasing the latch, may inadvertently damage either the calibration device or the catheter itself in one way or another.

For example, the free pivoting of the rocker arm may be impaired, the catheter-gripping device may be squeezed too tightly against the catheter, the cylindrical track in which the plunger operates may be deformed, or the plunger after release may be pushed too hard against the catheter tip. Although these consequences may all be unlikely, what is very likely is that if they do occur they will not be detected, and they will significantly alter the conditions of calibration.

The intermediate result is a concealed and probably systematic error in calibration—that is to say, one that will persist even if the calibration reading is continued for a protracted period, or even if several such readings are taken over a period of hours. The final result can be a serious misdiagnosis that has catastrophic effects for, e.g., a heart patient.

The final drawback introduced earlier is the placement of possibly conflicting constraints on the physical properties of the suspension medium. Shaw's patent suggests at several points—including the abstract and the claims—that the material must be, e.g., "compliant at the surface 14 and noncompressible" (column 4, lines 5 and 6).

These potentially inconsistent requirements are elsewhere expressed thus:

The mass of the reference element 17 should exhibit compliant characteristics at least at the surface to assure intimate optical engagement of the surface 14 of the reference element 17 with the ends or apertures of the optical fibers that are exposed at the distal tip 231 [of] the catheter 12. The incompressible characteristic of the mass is desirable to prevent changes in concentration of the uniformly dispersed particles 36 within the mass.

Yet another expression of the constraints on the suspension is this: "a solid medium that has a substantially incompressible body which is sufficiently compliant at its surface for intimate contact with the end of the light guide".

At the outset it is unclear whether an optimal calibration medium is nonuniform, or at least nonisotropic, in its properties—or whether it is possible for an entirely homogeneous substance to satisfy the requirements.

Shaw does not explain how much compliance "at the surface" can be accommodated before "changes in concentration ... within the mass" become excessive. Compliance, after all, is not truly a "surface" phenomenon but necessarily implicates the "body" or "mass" of the material.

Shaw does advise one skilled in the art to use "[s]ilicone resins which cure to a substantially transparent, *compliant and incompressible* solid mass" (emphasis added). This specification seems clearly to aggravate, rather than circumvent, the paradox just described.

Part of the dual requirement on Shaw's calibration medium arises from the dual way in which he uses the medium: first percussively, and then quantitatively. In other words, Shaw's catheter tip and calibration surface first must both survive the impact between them, and then are expected to act as well-behaved components of a high-precision measurement system.

Since it is not feasible in current technology to compromise the rigidity of the optical fibers in the catheter tip, all of the accommodation must be provided in the calibration surface.

If that surface were hard, then (1) upon impact it or the tip could crack or shatter, and (2) after impact it might not conform well to the optical surfaces to ensure a "liquid-like" optical engagement. On the other hand if the calibration mass were soft, then upon impact it could compress and throw off the calibration.

In this way of looking at things, the problem arises due to the impact, and one wonders whether it could be avoided simply by shipping the apparatus with the latch already released. Shaw's device, however, is plainly designed on the assumption that such a solution is unacceptable.

Otherwise the latch and release mechanisms could be simply omitted. The same is even more apparently true of his device that increases the lateral grip on the catheter body at the instant the release mechanism is triggered.

Shaw does not explain, and we can only speculate, whether he even thought of this solution, or if so then why he discarded it. One possibility is that Shaw was concerned about the effects of constant force on the catheter tip or the calibration medium, or both.

His device employs a spring to "urge" the calibration surface against the catheter tip. In very protracted pressing of the standard surface against the tip, either the mass of the calibration standard or the nonoptical bulk of the tip itself—the portion surrounding the fibers—would be likely to deform significantly.

The result could be problems of calibration or operation, or both kinds of problems. Anticipation of such problems is thus one possible reason for Shaw's "last minute" release mechanism and procedure. That mechanism and procedure, however, are precisely what produce the several drawbacks already pointed out.

The five problem areas just discussed all arise from a "blind spot" in the Shaw approach. That blind spot is essentially a natural inclination to emulate in a new hardware context the prior wet methods of calibration. A more sophisticated approach would recognize that such emulation is no longer necessary and would free the hardware configuration from purely historical constraints that produce the noted drawbacks. Such a solution would of course be highly desirable.

SUMMARY OF THE DISCLOSURE

Our invention is a disposable calibration medium and shipping sleeve for an optical catheter. The catheter is of the type that has a constriction near its tip. The catheter is further of a type that is adapted to project light from the interior of the catheter through the tip to the environment, and to receive light from the environment through the tip into the interior of the catheter.

The invention includes a body, and a cavity defined within the body to receive the tip of the catheter. The cavity fits sufficiently closely around the catheter to effectively prevent ambient light from reaching the tip.

The invention also includes some means for snapping into the constriction to gently retain the tip fully received within the cavity. For purposes of generality in expression we will refer to these means as "detent means." The detent means are defined within the cavity. They snap into the constriction only when the tip is received within the cavity fully.

In addition our invention includes some means for reflecting light that is projected outward from the interior of the optical catheter, back for reception into the interior of that same optical catheter.

These means, again for purposes of generality, we will call the "reflection means": they are within the cavity and generally facing the tip, in a mechanically and optically standardized relationship with the tip at all times—whenever the tip is fully received within the cavity.

The reflection means include a substance of standardized character and quality to provide a reflection standard for calibration. It will be noted that the substance is held passively in intimate contact with the tip of the catheter, without deforming stress.

Further, this condition continues (1) from the initial emplacement of the tip into the cavity of the calibration and shipping sleeve or boot (2) until the tip is removed from the sleeve for insertion into a patient's body.

Consequently the calibration of the tip may be performed as many times as desired, at any time between the initial emplacement and the eventual removal. In particular it may repeated, without the slightest inconvenience or compromise of reliability, at each waystation of shipment and at each benchmark of storage time, to maximize the likelihood of readiness for proper operation at the moment of use.

While the foregoing paragraphs may describe our invention in its most general terms, there are certain preferred features or characteristics which we consider advantageous to enhance the preparation or use, or both, of our invention.

In particular, we prefer that the substance be a substantially homogeneous suspension of reflecting particles in a material that is substantially translucent or transparent. The material is preferably a polymer, and preferably is molded with the suspended particles into a shape and size adapted to tightly grip the catheter.

We prefer that substantially the entire interior surface of the cavity be composed of the standardized substance. We also prefer that substantially the entire body be composed of the standardized subatance; in such a preferred form of the invention it may be advantageous to provide a separate external shell of a different substance—such as an opaque jacket.

As an alternative the entire body, including the interior surface but excluding the exterior surface, advantageously is composed of the standardized substance, and the exterior surface advantageously is substantially opaque.

Our invention also encompasses a method for shipping an optical catheter and preparing the catheter for operation. The method includes at least the following six steps.

One step is preparing a suspension of reflecting particles in an uncured polymeric material. Another step is causing to be prepared a mold that is shaped to form a body with a cavity that fits the catheter tip—sufficently closely around the catheter to effectively exclude ambient light from the tip.

Another step is placing the suspension in the mold. Yet another step is curing the polymeric material to form a body with a cavity of the character just described and to convert the suspension into a standardized reflecting substance for calibration of the tip.

Still another step is inserting the catheter tip into the cavity so that the tip enters and remains in a mechanically and optically standardized calibration juxtaposition with the standardized substance.

A final step is shipping the catheter tip and molded body together to a remote location for calibration and use; this step is performed while maintaining the standardized calibration juxtaposition.

By the use of this method, a user—upon receipt of the catheter at the remote location—can calibrate the catheter and tip using the standardized reflecting substance as it is already juxtaposed to the tip, and can then remove and discard the molded body to prepare the catheter for measurement use.

It is our preference, in regard to the method invention just described, that the causing and curing steps form the cavity to firmly grip the catheter—to obtain two advantageous results:

(1) during the shipping step, the catheter remains in stable position within the molded body to protect the catheter from shipping damage, and (2) during subsequent calibration by the user, the standardized reflecting substance is held in standardized position relative to the tip for proper calibration.

The catheter and calibration boot or sleeve are readily sealed in sterilized condition into a protective envelope for shipment. In effecting such sterilized sealing preparatory to shipment, optical connections at the proximal end of the catheter may be left exposed for calibration.

This may be accomplished, for example, by sealing the closure of the envelope around the body of the catheter near its proximal end. An outer enclosure, preferably repetitively reopenable and resealable to allow repeated recalibration whenever desired, may be provided outside the envelope and enclosing the optical connections.

All of the foregoing operational principles and advantages of the present invention will be more fully appreciated upon consideration of the following detailed description, with reference to the appended drawings, of which:

BRIEF DESCRIPTION OF THE DRAWINGS

FIG. 1 is a somewhat schematic general view, not to scale, of a preferred embodiment of our invention in place on the tip of an optical catheter that is attached to a typical optical-catheter system apparatus.

FIG. 2 is a longitudinal section, which may be considered to be a plan or elevation view, of one preferred form of the FIG. 1 embodiment.

FIG. 3 is an end elevation of the same embodiment, taken from the open end of the boot or sleeve.

FIG. 4 is a longitudinal section, similar to FIG. 2, of another preferred form of the FIG. 1 embodiment.

FIG. 5 is an external side plan or elevation of the tip of a catheter for use with our invention.

FIG. 6 is an external end elevation of the same catheter tip.

DETAILED DESCRIPTION OF THE PREFERRED EMBODIMENTS

As shown in FIG. 1, the disposable calibration sleeve and shipping boot 11 is positioned over the end (including the formed tip, FIG. 5) of an optical-type cardiovascular catheter 21. The catheter tip is inserted into the sleeve through an open end 18 and pushed in until it seats.

From comparison of FIGS. 2 and 5 it will be understood that there is a constriction 26 in the overall profile of the catheter 21, and that our invention provides a matching constriction 13, 14 in the internal wall of the sleeve/boot 11.

By "seats" we mean that the constriction 13, 14 in the internal wall of the sleeve 11 fits into the constriction 26 in the catheter. Preferably the fit is quite snug, so that the portion of the catheter tip distal to the constriction 26 is held in position firmly but gently.

Moreover, the internal dimensions of the distal end 15, 16 of the cavity 12 precisely match the external dimensions of the catheter tip—so that the extreme distal end of the catheter tip is held firmly but not forcibly against the end wall 16 (FIG. 2) of the sleeve 11.

The shape and size of the catheter constriction 25 can vary enormously with the design of the catheter 21. That design will in turn vary with the purposes for which the catheter is to be used, the size of the patient, and many other factors—not the least of which is the design philosophy of the manufacturer.

None of such variations is important to our invention, as long as (1) the catheter is of a type which has some constriction, though the constriction may be quite small, near its tip; and (2) the internal profile of the matching constriction inside our sleeve/boot 11 at least partially fits the constriction in the catheter.

Returning to FIG. 1, the proximal end of the catheter 21 typically is terminated in a connector manifold 22. Extending proximally from this manifold 22 are several individual hollow tubes and electrical extensions 23, and in particular a fiber-optic extension 24 with connector termination 25.

In use all of these several extensions 23, 24, 25 are connected to respective external devices for injecting or withdrawing fluids, electrical signals, and optical signals through the catheter. Of these several devices we illustrate in very schematic fashion only one that is particularly pertinent to the instant invention.

That is a device 43 which projects light through the optical-fiber means within the catheter 21 and out through the distal tips of those optical-fiber means. The device 43 also receives, detects and interprets light that is reflected back into the optical-fiber means from the environment of the tip.

By doing so the device 43 and the fiber-optic means within the catheter 21 cooperate to determine chemical characteristics (such as blood oxygen saturation) of that environment. As illustrated, the device 43 advantageously includes an optical-fiber means extension 42 of its own, terminating in a connector 41 that mates with the connector 25 from the catheter manifold 22.

Advantageously the catheter 21 after sterilization is enclosed for shipment in a sterile transparent bag 31, whose mouth is sealed by heat or otherwise along a marginal area 32. Preferably this marginal area is sealed around the fiber-optic extension 24, just distal to the fiber-optic connector 25—permitting passage of optical signals between the device 43 and the catheter tip, while maintaining a sterility-maintaining barrier 33 around the protruding fiber-optic extension 24.

The sterile bag 31 and protruding extension 24 and connector 25 are advantageously enclosed in a larger bag 34, which may preferably have a readily and repetitively reopenable and reclosable dust closure 36. This closure may, for example, be of the "snap locking" type.

In particular the closure 36 is advantageously of a type which can be opened only partially in a particular area, as at 37. Such a feature allows functional interconnection of the optical-fiber connectors 41 and 25 with minimal environmental exposure of the area near the sterility barrier 33 of the inner bag 31.

With suitable clean-room techniques, calibration can thus be checked any number of times without compromising the ultimate sterility of the catheter at use. This capability presents a real advance over the prior art.

Another advance over the prior art is that the person conducting a calibration need not handle the calibration boot/sleeve 11 through the bags 31, 34. The sleeve 11 is held with its internal calibration surface 16 (FIG. 2) securely but passively contacting the optical surfaces at the catheter tip, always ready for calibration.

Even a lengthy calibration-stability test of many hours or days could be performed without compromising the operability of the catheter in any way, should such a test become desirable.

The calibration boot/sleeve 11 may be of any convenient external shape, such as the cylindrical form illustrated in FIGS. 2 and 3. The cavity 12-16, accessible at only one end 18 of the body of the sleeve, has a proximal entrance section 12 that is cylindrical, if the exterior wall of the catheter is cylindrical.

Assuming the type of catheter tip illustrated in FIG. 5, the cylindrical entrance section 12 of the cavity may terminate in a conical section 13, which in turn leads to a cylindrical ledge 14 of substantially smaller diameter than the entrance section 12. Beyond this ledge 14 is a substantially spherical section 15. followed by a flat circular end wall 16.

The cavity constriction previously mentioned may now be seen to include not only the conical section 13 and the generally cylindrical ledge 13 but also the proximal portion of the spherical section 15. This constriction 13-15 and the constriction 26 (FIG. 5) near the catheter tip should fit together in such a way as to position the catheter tip very precisely adjacent to the reflectance standard surface 16.

Further, the boot/sleeve constriction 13-15, along with the body of the sleeve 11 generally, must be capable of deformation to permit the spherical tip section 27 of the catheter to pass through the constriction 13-15 of the cavity. Such passage is required for installation of the sleeve on the catheter—and again, upon application of mild tension between the catheter body and the sleeve 11, for removal of the sleeve immediately prior to use.

Within these constraints, however, the shapes of the cavity constriction 13-15 and catheter constriction 26 may depart very considerably. In particular, the constriction 13, 14, 15 need not fit all the way into the constriction 26 near the catheter tip, and their shapes need not be exactly complementary.

Other variables that are somewhat at the control of the designer, and which strongly affect the degree of match required or permitted, are the resiliency of the material 17 employed and the annular wall thickness of the cavity 12-16. The resiliency 17, however, in our design is primarily or even exclusively available for adjustment to the optimum value from the standpoint of optical coupling.

(Even the small forces that may be present with a very resilient calibration material can be avoided, if desired, by providing a small quantity of silicone oil or like optical-coupling substance between the catheter tip 136, F' and the calibration medium 16. The capability of such a substance to improve reproducibility in optical coupling by matching refractive indices is known.)

This very high degree of freedom to design the resiliency for optical optimization is another important advance which our invention offers. The significance of this advance will be particularly appreciated on review of the compromises that appear necessary in the prior art.

As shown in FIG. 4, if preferred a calibration boot and shipping sleeve 11' of our invention may be provided with an external shell 19. Such a shell may be used to improve opacity (for better exclusion of ambient light), mechanical security, or other properties as desired.

If desired the shell 19 may cover the proximal annular end 18' of the body of the sleeve, as illustrated. It may be either a chemical coating, as for example a kind of paint, or may be a separately formed element that is drawn or snapped into position over the material 17.

Although as mentioned earlier the thrust of our invention does not demand any particular kind of catheter, for reference it may be helpful to describe some features of one catheter tip with which our invention is particularly useful. FIGS. 5 and 6 represent the tip of such a catheter 21.

Fixed at the distal end of the catheter 21 are a molded tip 102 and an annular balloon 104. In the tip 102 is the polished distal end F' (FIG. 6) of a bundle of optical fibers that is drawn through a lumen in the catheter 21. Also in the tip 102 is a port or aperture D'.

This distal aperture D' effectively constitutes the distal end of another of the lumens in the catheter 21. The remaining space in the orifice of the tip is occupied with epoxy or like inert potting material 136.

As is well known in the cardiovascular field, a catheter of this general sort is inserted through the patient's vena cava into the right atrium and ventricle, with the tip 102 and its distal aperture D' extending onward into the patient's pulmonary artery. The tip 102 generally is held in that artery for pressure measurements there.

The balloon 104, as better seen in FIG. 5, is formed as a short length of latex tubing, positioned over a necked-down end section 131 of the catheter 21. The distal end of the balloon tubing 104 is doubled under and held by adhesive to the neck 103 of the tip 102.

The proximal end of the balloon tubing 104 is held by adhesive 135 to the proximal end of the necked-down end section 131, and the tapered annular space just proximal to the balloon is filled with epoxy or like cement. A very small balloon-inflation aperture B' is defined in the necked-down end section 131 of the catheter 101, communicating with the dedicated balloon lumen B.

From the point of view of our present invention, the most important feature of the tip of the catheter 21 is perhaps simply the constriction 26 that is formed at the neck 103 of the molded tip 102 proper. This constriction 26 lies between the doubled-under distal end of the balloon tubing 104 and the bulb 102.

The calibration boot or sleeve 11 of our invention is molded by injection or preferably (for greater control) compression from a two-part mixture—a base material and a reflective-particle filler. The filler is roughly one and one-half percent by weight of the mixture.

We are currently testing concentrations from one-quarter to one and one-quarter percent to determine the optimal value. It will be understood that this testing is straightforward. The criterion is reproducibility of the reflectance values obtained through the catheter. It is quite important that the concentration be uniform at the selected value.

The base material is advantageously a substantially transparent, medical-grade moldable high-strength silicone of durometer approximately thirty (using the scale known as "Shore A"). The filler is silica-free magnesium oxide (MgO) of ninety-nine percent purity, U.S.P. grade. It is obtained as a white powder with maximum particle size roughly one-thirtieth of a micron.

We have found it appropriate to provide three sizes of catheter—namely, diameters of five, six and seven "French". (The "French" is a customary unit of measure for catheter and needle diameters, one French being equal to a third of a millimeter.) Correspondingly the calibration sleeve/boot 11 of our invention is provided in three sizes.

In the smallest of these sizes, suitable with catheters designed for use with children, the diameter of the ledge 14 is 0.060 inch, that of the cylindrical entry section 12 of the cavity is 0.085 inch, that of the spherical portion 15 of the cavity is 0.073 inch, and that of the spherical, potting-material-filled end flat 136 is 0.025 inch.

The corresponding four values for a six-French catheter are 0.075, 0.120, 0.093 and 0.030 inch, and for a seven-French catheter 0.080, 0.120, 0.096, and 0.030 inch. Tolerances on these values are plus-or-minus approximately 0.003 inch, except for that on the cylindrical-section diameter—which may be 0.005 inch.

In all three sizes, the sleeve is one and a half inches long, and the center of the spherical portion 15 is at the center of the sleeve 11. The cone angle of the conical section 13 of the cavity is forty-five degrees plus or minus five degrees.

One vendor that is now able to produce such a molded part to specifications is Hi-Tech Rubber Inc., of Anaheim, Calif.

We prefer to provide a very precise abutment of the catheter tip and optical-fiber tips to the facing calibration surface. Recognizing, however, that there may sometimes be a slight positive clearance between the optically functional surfaces, we also prefer to provide a very small quantity of optical-coupling substance as a coating on the end structures of the catheter.

In particular, we consider it advantageous to add a one-percent solution of silicone oil in alcohol to such other liquid coating as may be applied on the distal structures of the catheter—e.g., to a heparin-complex solution that is often used to coat the balloon and pulmonary-artery distal aperture prior to shipment, to prevent formation of blood clots.

It will be understood that the foregoing disclosure is intended to be merely exemplary, and not to limit the scope of the invention—which is to be determined by reference to the appended claims.

We claim:

1. A disposable calibration medium and shipping sleeve for an optical catheter that has a tip and a constriction near the tip, such catheter being adapted for projection of light from the interior of such catheter through such tip to the environment of such tip and for reception of light from such environment through such tip into the interior of such catheter; said disposable medium and sleeve comprising:
    a body;
    a cavity, defined in the body, to receive such optical-catheter tip; said cavity fitting sufficiently closely around the catheter, when such tip is received within the cavity, to effectively prevent ambient light from reaching such tip;
    detent means, defined within the cavity, for snapping into the constriction when such tip is fully received within the cavity, to gently retain such tip fully received within the cavity; and
    means within the cavity and generally facing such tip and in a mechanically and optically standardized calibration relationship with such tip at all times, when such tip is fully received within the cavity, for reflecting such light projected from the interior of such catheter back for reception into the interior of such catheter;
    said reflection means comprising a substance of standardized character and quality to provide a reflection standard for calibration.

2. The disposable medium and sleeve of claim 1, wherein:
    the cavity has an interior surface; and
    substantially the entire interior surface is composed of said standardized substance.

3. The disposable medium and sleeve of claim 1, wherein:
    the cavity has an interior surface; and
    substantially the entire body, including the interior surface of the cavity, is composed of said standardized substance.

4. The disposable medium and sleeve of claim 1, wherein:
    the body has an exterior surface;
    the cavity has an interior surface;
    substantially the entire body, including the interior surface of the cavity but excluding the exterior surface of the body, is composed of said standardized substance; and
    the exterior surface of the body is substantially opaque.

5. The disposable medium and sleeve of claim 1, wherein:
    the substance is a substantially homogeneous suspension of reflecting particles.

6. The disposable medium and sleeve of claim 4, wherein:
    the particles are suspended in a material that is substantially translucent or transparent.

7. The disposable medium and sleeve of claim 5, wherein:
    the material is a polymer.

8. The disposable medium and sleeve of claim 1, further comprising:
    a quantity of generally transparent liquid interposed between such tip and said substance, when such tip is received within the cavity.

9. The disposable medium and sleeve of claim 1, wherein:
    the body and its cavity are molded from a suspension of particles in a generally translucent or transparent polymer.

10. The disposable medium and sleeve of claim 1, wherein:
    the body and its cavity are shaped, sized and adapted to tightly grip such catheter, when such tip is received within the cavity.

11. The disposable medium and sleeve of claim 10, wherein:
    the body and its cavity are molded from a suspension of particles in a generally translucent or transparent polymer.

12. A method for shipping and preparing for calibration an optical catheter that has a tip, such catheter being adapted for projection of light from the interior of such catheter through such tip to the environment of such tip and for reception of light from such environment through such tip into the interior of such catheter; said method comprising the steps of:
    preparing a suspension of reflecting particles in an uncured polymeric material;
    causing to be prepared a mold that is shaped to form a body with a cavity that fits such catheter tip sufficiently closely around the catheter to effectively prevent ambient light from reaching such tip;

placing said suspension in the mold;

curing said polymeric material to form a body with a cavity that fits such catheter tip sufficiently closely around the catheter to effectively prevent ambient light from reaching such tip, and to convert said suspension into a standardized reflecting substance for calibration of such tip;

inserting such catheter tip into the cavity so that such tip enters and remains in a mechanically and optically standardized calibration juxtaposition with the standardized substance; and while maintaining the standardized calibration juxtaposition, shipping such catheter tip and molded body together to a remote location for calibration and use;

whereby, upon receipt at such remote location, a user can calibrate such catheter and tip using the standardized reflecting substance as it is already juxtaposed to such tip, and can then remove and discard the molded body to prepare the catheter for measurement use.

13. The method of claim 12, wherein:

the causing and curing steps form the cavity to firmly grip such catheter;

whereby during the shipping step such catheter remains in stable position within the molded body to protect such catheter from shipping damage; and during subsequent calibration by such a user the standardizd reflecting substance is held in standardized position relative to such tip for proper calibration.

* * * * *